US00PP14503P29

(12) United States Plant Patent
Harrison

(10) Patent No.: US PP14,503 P2
(45) Date of Patent: Feb. 3, 2004

(54) DIASCIA PLANT NAMED 'ICEPOLE'

(50) Latin Name: *Diascia×hybrida*
Varietal Denomination: Icepole

(76) Inventor: Hector Harrison, deceased, late of Scunthorpe (GB), by Joyce Gertrude Harrison, administrator ( * ) Notice: Subject to any disclaimer, the term of this patent is extended or adjusted under 35 U.S.C. 154(b) by 0 days.

(21) Appl. No.: 10/109,906

(22) Filed: Mar. 29, 2002

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of Diascia plant named 'Icepole', characterized by its upright and somewhat outwardly spreading plant habit; freely branching habit; freely and continuous flowering habit; and white-colored flowers.

1 Drawing Sheet

Botanical classification/cultivar designation: *Diascia×hybrida* cultivar Icepole.

BACKGROUND OF THE INVENTION

The present Invention relates to a new and distinct cultivar of Diascia plant, botanically known as *Diascia×hybrida,* and hereinafter referred to by the cultivar name Icepole.

The new Diascia is a product of a planned breeding program conducted by the Inventor in Appleby, Scunthorpe, North Lincolnshire, United Kingdom. The objective of the breeding program is to create new Diascias with good plant vigor and numerous flowers with attractive coloration.

The new Diascia originated from a cross made by the Inventor in 1996 of a proprietary selection of *Diascia× hybrida*identified as code number 96L2, not patented, as the female, or seed parent, with the *Diascia×hybrida* cultivar Ice Cracker, not patented, as the male, or pollen parent. The new Diascia was selected as a single plant from the resulting progeny by the Inventor in 1997, in Appleby, Scunthorpe, North Lincolnshire, United Kingdom on the basis of its plant habit and attractive flower color.

Asexual reproduction of the new cultivar by cuttings taken in Appleby, Scunthorpe, North Lincolnshire, United Kingdom since 1997 has shown that the unique features of this new Diascia are stable and reproduced true to type in successive generations.

SUMMARY OF THE INVENTION

Plants of the cultivar Icepole have not been observed under all possible environmental conditions. The phenotype may vary somewhat with variations in environment such as temperature and light intensity without, however, any variance in genotype.

The following traits have been repeatedly observed and are determined to be the unique characteristics of 'Icepole'. These characteristics in combination distinguish 'Icepole' as a new and distinct Diascia cultivar:

1. Upright and somewhat outwardly spreading plant habit.
2. Freely branching habit.
3. Freely and continuous flowering habit.
4. White-colored flowers.

Plants of the new Diascia are most similar to plants of the parent selection and cultivar. Plants of the new Diascia differ from plants of the parent selection and cultivar primarily in flower color as flower color of plants of the new Diascia is more intense. In addition, plants of the new Diascia have a more uniform plant habit than plants of the parent selection and cultivar.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs differ slightly from the color values cited in the detailed botanical description which accurately describe the colors of the new Diascia.

The photograph at the top of the sheet comprises a side perspective view of three typical flowering plants of 'Icepole' grown in a 20-cm container.

The photograph at the bottom of the sheet comprises a close-up view of typical leaves, flowering stems, developing flowers, and fully opened flowers of 'Icepole'.

DETAILED BOTANICAL DESCRIPTION

The aforementioned photographs and following observations and measurements describe plants grown in Bonsall, Calif., in an outdoor nursery under full sunlight conditions during the summer with day temperatures ranging from 18 to 35° C. and night temperatures ranging from 7 to 18° C. Plants were grown for about six weeks in 20-cm containers with three plants per container. Color references are made to The Royal Horticultural Society Colour Chart, 1995 Edition, except where general terms of ordinary dictionary significance are used.

Botanical classification: *Diascia×hybrida* cultivar Icepole.
Parentage:

*Female parent.*—Proprietary selection of *Diascia× hybrida* identified as code number 96L2, not patented.

*Male parent.*—*Diascia×hybrida* cultivar Ice Cracker, not patented.

Propagation:

*Type.*—By cuttings.

*Time to initiate roots.*—About 7 days at 8 to 12° C.

*Time to produce a rooted young plant.*—About 14 to 20 days at 8 to 12° C.

*Root description.*—Fine and fibrous.

*Rooting habit.*—Freely branching.

Plant description:

*Form.*—Upright and somewhat outwardly spreading; rounded with mounded crown. Very freely branching; about 40 lateral branches per plant. Vigorous growth habit.

*Plant height.*—About 28 cm.

*Plant diameter* (*spread*).—Single plants: About 30 cm. Three plants: About 58 cm.

*Lateral branches.*—Length: About 30 cm. Diameter: About 2 mm. Internode length: About 2.5 to 4.5 cm. Cross-section: Square. Orientation: Initially upright, then outwardly arching to somewhat trailing and decumbent. Strength: Moderately strong. Texture: Smooth, glabrous. Color: 144A.

*Foliage description.*—Arrangement: Opposite; simple. Quantity per lateral branch: About 20. Length: About 2.3 cm. Width: About 1.7 cm. Shape: Deltoid. Apex: Broadly acute. Base: Truncate. Margin: Slightly serrate. Texture, upper and lower surfaces: Smooth, glabrous. Venation pattern: Pinnate. Color: Young foliage, upper surface: 146A. Young foliage, lower surface: 147C. Fully expanded foliage, upper surface: 144A. Fully expanded foliage, lower surface: 146B. Venation, upper surface: 144A. Venation, lower surface: 146B. Petioles: Length: About 3 mm. Diameter: About 2 mm. Texture: Smooth, glabrous. Color: 144B.

Flower description:

*Flower type and habit.*—Single flowers borne on short terminal racemes; flowers zygomorphic. Five modified petals fused at base: two upper (banner) petals, two lateral petals with nectar spurs and one larger lower lip petal. Flowers not persistent. Very freely flowering; typically more than 2,000 flowers develop per plant during the flowering season. Flowers face upright or outward.

*Natural flowering season.*—Plants typically flower from March through June in the Northern Hemisphere; flowering continuous during this period.

*Flower longevity on the plant.*—About 2 to 4 days.

*Fragrance.*—None detected.

*Raceme height.*—About 8 to 11 cm.

*Raceme diameter.*—About 3.5 cm.

*Flowers size.*—Diameter: About 2 by 2 cm. Depth (height): About 8 mm.

*Flower buds* (*showing color*).—Length: About 7 mm. Diameter: About 6 mm. Shape: Oval. Color: 155A.

*Petals.*—Quantity/arrangement: Five modified petals fused at base: two upper (banner) petals, two lateral petals and one larger lower lip petal. Base of banner petals with indented yellow eyespots; lower surfaces of lateral petals modified into nectar spurs; and lower lip petal convex forming horizontal insect landing platform. Length: Banner petals: About 4 mm. Lateral petals: About 5 mm. Lower lip petal: About 8 mm. Width: Banner petals: About 6 mm. Lateral petals: About 6 mm. Lower lip petal: About 1 cm. Lateral petal spur: Length: About 7 mm. Diameter, at petal attachment: About 2 mm. Shape, all petals: Roughly spatulate. Apex, all petals: Rounded. Margin, all petals: Entire. Texture, all petals, upper and lower surfaces: Smooth, velvety. Color, all petals: Upper and lower surfaces, when opening: 155B. Upper and lower surfaces, fully opened: 155D; tiny spots at base of petals, 52A. Eyespot on banner petals: 7A. Nectar spurs: 155D.

*Sepals.*—Arrangement/appearance: Single whorl of five sepals fused at base; star-shaped. Length: About 4 mm. Width: About 1.5 mm. Shape: Narrowly elliptic. Apex: Acute. Margin: Entire. Texture, upper and lower surfaces: Smooth, glabrous. Color, immature, upper and lower surfaces: 144A. Color, mature, upper and lower surfaces: 144A.

*Peduncles.*—Length: About 5 cm. Diameter: About 1.5 mm. Angle: Erect to about 45° from the stem. Strength: Moderately strong. Texture: Smooth, glabrous. Color: 144A.

*Pedicels.*—Length: About 1.4 cm. Diameter: Less than 1 mm. Angle: About 45° from the stem. Strength: Moderately strong; slender. Texture: Smooth, glabrous. Color: 144B.

*Reproductive organs.*—Stamens: Quantity per flower: Four. Anther shape: Ovoid. Anther length: Less than 1 mm. Anther color: 14A. Pollen amount: Scarce. Pollen color: 14A. Pistils: Quantity per flower: One. Pistil length: About 4 mm. Style length: About 2 mm. Style color: 144C. Stigma shape: Rounded. Stigma color: 144C. Ovary color: 144C.

*Seed/fruit.*—Seed nor fruit production has not been observed.

Disease/pest resistance: Plants of the new Diascia have not been noted to be resistant to pathogens or pests common to Diascia.

Temperature tolerance: Plants of the new Diascia have been observed to tolerate temperatures from −4 to 38° C.

It is claimed:

1. A new and distinct cultivar of Diascia plant named 'Icepole', as illustrated and described.

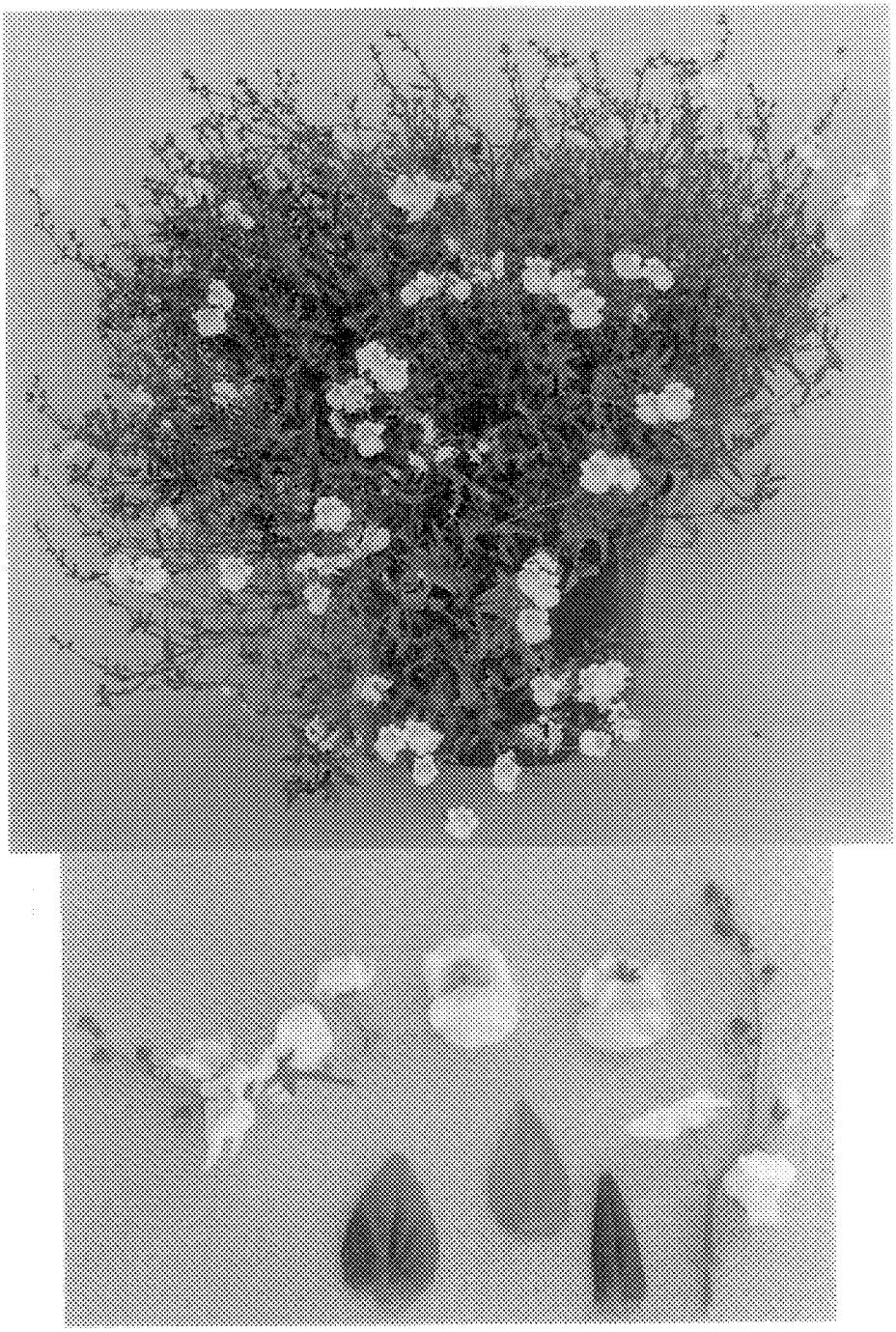

* * * * *